United States Patent [19]

King et al.

[11] Patent Number: 5,523,477
[45] Date of Patent: Jun. 4, 1996

[54] PROCESS FOR THE PREPARATION OF 1-(THIOMETHYL)-CYCLOPROPANEACETIC ACID

[75] Inventors: Steven King, Summit; Brenda Pipik, Edison; David A. Conlon, Plansboro, all of N.J.

[73] Assignee: Merck & Co., Inc., Rahway, N.J.

[21] Appl. No.: 376,715

[22] Filed: Jan. 23, 1995

[51] Int. Cl.$^6$ .................................................. C07C 61/04
[52] U.S. Cl. .............................. 562/506; 549/15; 558/347
[58] Field of Search ..................... 549/15, 18; 558/347; 562/506

[56] References Cited

U.S. PATENT DOCUMENTS

| | | | |
|---|---|---|---|
| 4,596,879 | 6/1986 | Fizet | 549/18 |
| 5,270,324 | 12/1993 | Zamboni et al. | |
| 5,350,760 | 9/1994 | LaBelle | 514/367 |
| 5,438,141 | 8/1995 | LaBelle | 546/176 |

FOREIGN PATENT DOCUMENTS

| | | |
|---|---|---|
| 0480717 | 4/1992 | European Pat. Off. |
| 0604114 | 6/1994 | European Pat. Off. |

OTHER PUBLICATIONS

U.S. Ser. No. 08/350,428 Dec. 9, 1994, to McNamara et al. (Case 19156IA).

*Primary Examiner*—Michael L. Shippen
*Attorney, Agent, or Firm*—Mollie M. Yang; David L. Rose

[57] ABSTRACT

The present invention provides a novel process for the preparation of 1,1-cyclopropanedimethanol cyclic sulfite which comprises: (a) contacting 1,1-cyclopropanedimethanol with dialkylsulfite in the presence of a base; and (b) removing from the reaction mixture the alcohol reaction by-product. This process is incorporated in the additional novel processes for preparing 1-(hydroxymethyl)cyclopropaneacetonitrile and 1-(thiomethyl)cyclopropaneacetic acid.

16 Claims, No Drawings

PROCESS FOR THE PREPARATION OF 1-(THIOMETHYL)-CYCLOPROPANEACETIC ACID

BACKGROUND OF THE INVENTION

The leukotrienes constitute a group of locally acting hormones, produced in living systems from arachidonic acid. The major leukotrienes are Leukotriene B4 (abbreviated as LTB4), LTC4, LTD4, and LTE4. The biosynthesis of these leukotrienes begins with the action of the enzyme 5-lipoxygenase on arachidonic acid to produce the epoxide known as Leukotriene A4 (LTA4), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various disease states are also discussed in the book by Rokach.

Recently a number of compounds of formula (1) in which A represents optionally substituted heterocycle, and pharmaceutically acceptable salts thereof, have been disclosed as leukotriene antagonists and inhibitors of leukotriene biosynthesis.

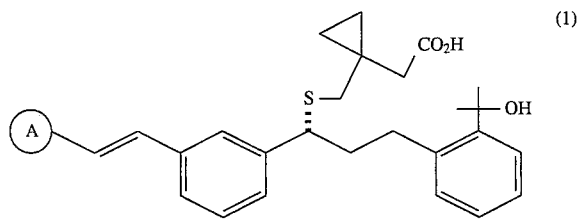

(1)

EP 480,717 discloses compounds of formula (1) in which A represents optionally substituted quinoline; more specifically disclosed is the compound in which A represents 7-chloro-2-quinolinyl. U.S. Pat. No. 5,270,324 discloses two compounds of formula (1) in which A represents 6-fluoro- or 6,7-difluoro-2-quinolinyl. In EP 604,114 there is disclosed compounds in which A is halo-substituted thieno[2,3-b]pyridine, particularly 2,3-dichlorothieno[2,3-b]pyridin-5-yl. Compounds of formula (1) are useful in the treatment of asthma as well as other conditions mediated by leukotrienes, such as inflammation and allergies.

In the afore-mentioned references, the thiomethylcyclopropaneacetic acid moiety of compounds of formula (1) is introduced using methyl 1-(thiomethyl)cyclopropaneacetate. While in EP 480,717 methyl 1-(thiomethyl)cyclopropaneacetate is prepared from 1,1-cyclopropanedimethanol by stepwise transformation of the two hydroxy groups into the thiol and carboxylate moieties, an improved synthesis is used in U.S. Pat. No. 5,270,324 and EP 604,114, which involves first converting 1,1-cyclopropanedimethanol into the corresponding cyclic sulfite using thionyl chloride.

Subsequently, it has been discovered that 1-(thiomethyl)cyclopropaneacetic acid can be prepared from 1-(acetylthiomethyl)cyclopropaneacetonitrile by conducting the hydrolysis in a biphasic system, the product may then be crystallized from a hydrocarbon such as hexane or heptane. The dilithium salt of 1-(thiomethyl)cyclopropaneacetic acid, generated in situ, is used in the preparation of compounds of formula (1).

In the previous process for preparing 1-(thiomethyl)cyclopropaneacetic acid, the method for preparing cyclic sulfite results in a number of by-products thereby reducing the yield of the desired cyclic sulfite; the process also requires multiple aqueous extractions, and solvent switches rendering it difficult to adapt to large scale production. Accordingly, there exists the need for an efficient synthesis of 1-(thiomethyl)cyclopropaneacetic acid which is amenable to scale-up, and provides improved overall product yield.

SUMMARY OF THE INVENTION

The present invention relates to a novel process for the preparation of 1,1-cyclopropanedimethanol cyclic sulfite, 1-(hydroxymethyl)cyclopropaneacetonitrile acid, and 1-(thiomethyl)cyclopropaneacetic acid.

DETAILED DESCRIPTION OF THE INVENTION

The following abbreviations and terms have the indicated meanings.

diol=1,1-cyclopropanedimethanol

DMF=dimethylformamide hydroxy nitrile=1-(hydroxymethyl)cyclopropaneacetonitrile thioacetate nitrile=1-(acetylthiomethyl)cyclopropaneacetonitrile thol acid=1-(thiomethyl)cyclopropaneacetic acid In one aspect the present invention provides a process for the preparation of the compound 1,1-cyclopropanedimethanol cyclic sulfite having the formula

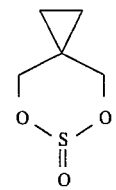

which comprises: (a) contacting 1,1-cyclopropanedimethanol with dialkylsulfite in the presence of a base or an acid; and (b) removing from the reaction mixture the alcohol reaction by-product. Preferably, the reaction is conducted under basic conditions. The term "alkyl" as used herein encompasses branched or straight carbon chains having from 1 to 6 carbon atoms, and carbocycles of 3 to 6 carbon atoms.

The starting materials are compounds known in the art and may be readily prepared according to known processes. The dialkylsulfite may be for example dimethyl-, diethyl- or diisopropylsulfite, the preferred being diisopropylsulfite. The diol is preferably dried (e.g. to a KF of <200 µg/mL) prior to being used in the reaction; drying can be conveniently achieved by azeotroping the diol in DMF. The reaction may be either acid-catalyzed or base-catalyzed. Suitable acids are for example sulfonic acids such as toluenesulfonic acid, methanesulfonic acid, benzenesulfonic acid and the like. As previously mentioned, the reaction is preferably catalyzed by a base. The base may be a hydroxide or an alkoxide wherein the couterion is a Group IA metal such as lithium, sodium or potassium, or a Group IIA metal such as calcium or magnesium; a preferred base is sodium t-butoxide.

The reaction is conducted in inert organic solvent such as aromatic hydrocarbons (e.g. toluene), ethers (e.g. tetrahydrofuran), or amides (e.g. dimethylformamide), or a mixture thereof; a preferred solvent is DMF. The amount of dialkylsulfite used is approximately equal to that of the diol, but preferably a slight excess (e.g. about 1.2 equivalents) of the dialkylsulfite is used. The base is typically used in catalytic amount of about 1.5 to about 5 mole % relative to the diol.

The reaction by-product, an alcohol such as isopropanol, is removed to promote product formation. Removal of the alcohol may be achieved by distillation at a temperature of about 35° to about 75° C., and at a pressure of about 30 to about 100 torr.

In a preferred embodiment of the process, the dialkylsulfite is diisopropylsulfite, the base is sodium t-butoxide, and the reaction is carried out in DMF. Since sodium t-butoxide slowly decomposes during distillation to remove isopropanol, the base is preferably added in portions; for example, 1.6 mole % may be added initially, and when the boiling point of the reaction mixture exceeds 70° C. addtional 0.8 mole % and then 0.4 mole % portions may be added. Our experience shows that 99% of the isopropanol can be removed with a total base of 2.8 mole % added over 2 to 5 hours of distillation at 50 torr. The course of the reaction may be followed by conventional chromatographic or spectroscopic techniques. Distillation is discontinued when less than 0.5% of the diol (relative to the cyclic sulfite) remains. The presence of the base in the reaction mixture may adversely affect the product yield of the hydroxy nitrile in the next step; therefore, the reaction mixture is preferably kept at 70° C. for 1 hour to ensure destruction of the base.

In a second aspect the present invention provides a process for the preparation of 1-(hydroxymethyl)cyclopropaneacetonitrile which comprises: (a) contacting 1,1-cyclopropanedimethanol with dialkylsulfite in an inert polar organic solvent and in the presence of a base; (b) removing from the reaction mixture the alcohol reaction by-product; and (c) adding directly to the product of step (b) sodium cyanide and sodium iodide to provide the desired product. Steps (a) and (b) are essentially as described in detail above, with the further limitation that the reaction be carried out in an inert polar organic solvent, preferably DMF. The yield of the hydroxy nitrile may decrease in the presence of the base, or an excess amount of the diol or isopropanol, it is therefore preferred that the reaction mixture after step (b) contains less than 0.5 mole % of the diol and less than 2 mole % of isopropanol relative to cyclic sulfite, and that essentially all the base is destroyed.

The reaction mixture obtained in step (b) is directly treated with the cyanating reagents, i.e. the cyclic sulfite of step (b) is not isolated, and the the solvent of the previous steps is not changed. The yield of the hydroxy nitrile is increased when dry sodium cyanide and dry sodium iodide are used in step (c); thus preferably sodium cyanide having water content of <0.5% and sodium iodide having water content of <0.5% are used. The amount of sodium cyanide used is approximately equal to that of the cyclic sulfite, but preferably sodium cyanide is used in slight excess, e.g. about 1.1 equivalents. Sodium iodide is generally used in catalytic amount of up to 0.5 equivalents, but typically about 0.2 equivalents is used. The reaction is carried out at elevated temperature, for example from about 50° to about 110° C. preferably at about 70° C. The reaction is complete within about 10 to about 50 hours, typically in about 40 hours.

In another aspect the present invention provides a process for the preparation of 1-(thiomethyl)cyclopropaneacetic acid which comprises: (a) contacting 1,1-cyclopropanedimethanol with dialkylsulfite in an inert polar organic solvent and in the presence of a base; (b) removing from the reaction mixture the alcohol reaction by-product; (c) adding directly to the product of step (b) sodium cyanide and sodium iodide to provide 1-(hydroxymethyl)cyclopropaneacetonitrile; (d) converting the hydroxy group of the product of step (c) into a sulfonate leaving group; (e) contacting the product of step (d) with thiolacetic acid and an amine base to provide 1-(acetylthiomethyl)cyclopropaneacetonitrile; and (f) hydrolyzing the product of step (e) in a biphasic solvent system to provide the desired product.

Steps (a) through (c) have been described in detail above. For the preparation of 1-(thiomethyl)cyclopropaneacetic acid, the product obtained from step (c), i.e. 1-(hydroxymethyl)cyclopropaneacetic acid is converted into a corresponding sulfonate such as the methanesulfonate or toluenesulfonate. Thus, the hydroxy nitrile is treated with a sulfonylating agent such as methanesulfonyl chloride or toluenesulfonyl chloride, in the presence of an organic amine base, a preferred base being triethylamine. The amounts of the sulfonylating agent and the base used are approximately equal to that of the hydroxy nitrile, but typically they are used in slight excess, e.g. about 1.1 to about 1.5 equivalents.

The reaction is conducted in an inert organic solvent; suitable solvents may be for example, hydrocarbons such as pentane, hexane, heptane and the like; aromatic hydrocarbons such as benzene, toluene, xylene and the like; ethers such as tetrahydrofuran. Preferably, the reaction is carried out in a solvent mixture containing the solvent from the previous step; more preferably, the solvent mixture is toluene/DMF. When toluene/DMF is used, the ratio of toluene: DMF should be at least 1.9:1. Typically, the sulfonylation is run in a toluene/DMF mixture having a ratio of about 2.4:1 to about 3:1. The reaction is carded out at a temperature of from about −40° to about 40° C., typically the reaction temperature is maintained at or below 5° C.

The reaction mixture containing the sulfonate is then treated with a source of thioacetate, for example potassium thioacetate or triethylammonium thioacetate, to provide 1-(acetylthiomethyl)cyclopropaneacetic acid. Triethylammonium thioacetate, the preferred agent, may be generated in situ using triethylamine and thiolacetic acid. The reaction is carried out at a temperature of about 10° to about 80° C., typically at about 35° C. The reaction is substantially complete within about 10 hours.

The thioacetate nitrile obtained above is subsequently converted into 1-(thiomethyl)cyclopropaneacetic acid via base-catalyzed hydrolysis in a biphasic solvent system. It has been found that hydrolysis carried out in water results in a significant amount of impurity. The amount of impurity in the reaction mixture is substantially reduced when the hydrolysis is carded out in a biphasic system containing an organic solvent and water. In the biphasic hydrolysis the desired intermediate, the thiolate of 1-(thiomethyl)cyclopropaneacetonitrile, is contained in the aqueous layer while neutral impurities remain in the organic layer, and are thus easily removed. In addition, crude thioacetate nitrile may be used in the biphasic hydrolysis thereby avoiding the need for chromatographic purification.

Thus a mixture of the thioacetate nitrile in an organic solvent and an aqueous of a base such as sodium hydroxide is stirred at ambient temperature to provide the sodium thiolate of 1-(thiomethyl)cyclopropane-acetonitrile. Suitable organic solvents are for example aromatic hydrocarbons such as toluene, xylenes, and the like; the preferred organic solvent is toluene. The reaction may be carried out at a temperature ranging from room temperature to reflux point of the reaction mixture. Preferably, the biphasic mixture is maintained at room temperature until the starting material has been substantially consumed, typically in about 6 to 18 hours.

The aqueous solution containing the intermediate, the sodium thiolate of 1-(thiomethyl)cyclopropaneacetonitrile, is separated from the organic layer containing unwanted impurities. The aqueous solution is maintained at elevated temperature up to the reflux point to convert the thiolate into 1-(thiomethyl)cyclopropaneacetic acid disodium salt, e.g. at 80° C. to about 90° C. for about 12 to 16 hours. An organic solvent such as toluene or heptane is then added to the aqueous solution and the mixture acidified to pH 3.5 to 4. The organic layer containing the thiol acid is separated. In a preferred embodiment the solvent is heptane.

Thus, a mixture of the thiol acid in heptane is warmed to 34° C. to completely solubilize the compound, and allowed to slowly cool to about 25° C. over 1 hour. Seeding the mixture with crystals of the thiol acid may be used to accelerate crystal formation. The mixture is further cooled to about −5° C. over about 3 hours for crystal formation.

1-(Thiomethyl)cyclopropaneacetic acid is used in the preparation of compounds of formula (1); more particularly, it is used in the preparation of a compound of formula (1) in which A represents 7-chloro-2-quinolinyl. Thus, the thiol acid is first converted into the dilithium dianion by contacting the former with a lithium base such as n-butyl lithium in hexane or heptane, and the like. The reaction is carded out in an inert organic solvent such as THF, toluene or a mixture thereof, and at a temperature of below 0° C., typically at about −5° C. or lower.

A sulfonate of formula (2), wherein L is for example methanesulfonyl and A has the meanings under formula (1), is then added to the solution of the dilithium dianion.

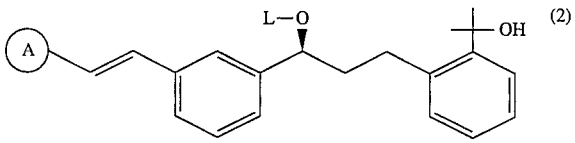

The sulfonate may be added directly as a solid, or in solution in an inert organic solvent such as THF or toluene, preferably THF. Since the sulfonate (2) has limited stability in solution, the sulfonate solution is preferably prepared just prior to addition to the dianion solution, and in any case is best used within about 30 minutes.

The reaction mixture is maintained at below about 0° C., generally at about −5° C. until completion of the reaction, typically the reaction is complete within about 10 hours. The reaction solution containing the desired product is then treated with a water soluble carboxylic acid, e.g. acetic acid, oxalic acid, tartaric acid and the like to provide the free acid form of a compound of formula (1); a preferred carboxylic acid is tartaric acid.

A compound of formula (1) as obtained above may be convened to the dicyclohexylamine (DCHA) salt. Thus dicyclohexylamine is added to a solution of a compound of formula (1) in ethyl acetate, followed by hexanes to effect crystallization of the dicyclohexylamine salt. Preferred ratio of ethyl acetate:hexanes is about 1:1 to about 1:2. A seed of the dicyclohexylamine salt is preferably added to the ethyl acetate/hexane solution to accelerate crystal formation. The dicyclohexylamine salts crystallize as needles.

A second crystalline form of the DCHA salt of a compound of formula (I) may be obtained by crystallization from toluene/heptane. Thus, the free acid of a compound of formula (I) in an organic solvent such as THF is treated with dicyclohexylamine; toluene is then added and the solution concentrated to remove the THF. After dilution with additional toluene, heptane is added to the toluene solution. The ratio of toluene:heptane is about 2:1 to about 3:1. The crystallization may be accelerated by the addition of DCHA salt seeds previously obtained from toluene/heptane.

The readily isolable crystalline dicyclohexylamine salt, in either form, offers a simple and efficient method for the purification of a compound of formula (1), thereby circumventing the need for tedious chromatographic purification and resulting in higher product yields. The dicyclohexylamine salt is then converted to the free acid or a pharmaceutically acceptable salt using conventional procedures; for example treatment with acetic acid followed by sodium hydroxide provides the sodium salt of a compound of formula (1).

The following examples are provided to more fully illustrate the present invention. The examples are not meant to limit the scope of the claims, which is solely defined by the claims, in any manner.

EXAMPLE 1

Preparation of 1-(mercaptomethyl)cyclopropaneacetic acid

Step 1: Diisopropyl sulfite

Toluene (500 mL) and isopropanol (306 mL, 4 mole) were combined under nitrogen in a 2 L flask equipped with a dropping funnel and thermocouple, Thionyl chloride (73 mL, 1 mole) was added from the dropping funnel over 30 minutes maintaining the temperature at 15°–25° C. When the addition was complete, the reaction mixture was put under vacuum to remove HCl. Vigorous HCl evolution was noted at 150 mm.

The pressure was lowered slowly. When gas evolution ceased, the mixture was concentrated to remove toluene and excess isopropanol. Concentration was continued until less than 1% isopropanol remained. Yield=159 g, 95%. Triethylamine (1 mL) was added to stabilize the product and the incipient precipitate was filtered away. The solution was used as is.

Step 2: 1-(Hydroxymethyl)cyclopropaneacetonitrile

Dimethylformamide (225 mL) and 1,1-cyclopropanedimethanol (26.6 g; at 95 wt %, actual amount=25.5 g, 250 mmol) were placed in a 1 L flask equipped with a vacuum distillation apparatus. DMF (25 ml) was distilled at 75° C./50 torr, and to the remaining solution was added a solution of diisopropyl sulfite in toluene (81.6 mL, 49.9 g, 300 mmol). Toluene (50 mL) was distilled at 52° C./55 torr, and the resulting solution had a KF of 98 µg/mL.

Sodium t-butoxide, (2M in tetrahydrofuran, 2.0 mL) was added, and distillation was begun again at 35° C./50 torr, with 30 mL of distillate collected. Distillation was continued to collect 60 mL at 50°–70° C./50 torr. Sodium t-butoxide (1.0 mL) was added and the distillation was continued to collect 60 mL of distillate at 60°–75° C./50 torr. After the addition of more sodium t-butoxide (0.5 mL), and distillation of 30 mL at 70°–75° C./50 torr, the distillation was stopped, and the mixture was maintained at 70° C. for 1 h and then cooled to room temperature. The yield of 1,1-cyclopropanedimethanol cyclic sulfite=33.0 g, 89%.

Sodium cyanide (13.5 g, 275 mmol) and sodium iodide (7.5 g, 50 mmol) were added to the solution obtained above, and the heterogeneous mixture was slowly warmed over 1 h to 70° C., and aged for about 40 h with vigorous stirring. Toluene (400 mL) was added slowly at 70° C., and then water (6 mL) was added dropwise over 30 minutes. The mixture was then dried by vacuum distilling 100 mL of toluene; when the KF of the mixture was 200 µg/mL, it was cooled to 10° C. and filtered. The precipitate was washed with toluene (100 mL), and the combined filtrate contained 21.4 g of the title compound (77% from 1,1-cyclopropyldimethanol).

Step 3: 1-(Acetylthiomethyl)cyclopropaneacetonitrile

The product of Step 2 in toluene/DMF (3:1) (210 mL for 34.2 g of the product compound) and triethylamine (55.8 mL, 0.4 mol) were combined in a 3-neck 1 L round bottom flask equipped with mechanical stirring and a thermocouple, flushed with nitrogen and cooled to −15° C. Mesyl chloride (26.3 mL, 0.389 mmol) was added dropwise over 3 h, keeping the temperature below +5° C.

Triethylamine (64.4 mL) and thioacetic acid (26.4 mL, 0.37 mole) were added sequentially as quickly as possible; the mixture was removed from the cooling bath and heated to 35° C. This temperature was maintained until <1% of the mesylate remained (about 7 h). Water (250 mL) was added, the mixture was shaken, and the two phases were separated. The aqueous phase was extracted with toluene (200 mL), and the organic phases were combined. The combined organic phases (470 mL) contained 48.3 g (93%) of the desired product.

Step 4: 1-Mercaptomethyl)cyclopropaneacetic acid

The product solution of Step 3 (447 g containing 48 g of the product compound) was washed with deionized water (2×150 mL). In a 1 L three-neck flask equipped with nitrogen inlet and mechanical stirring, the organic layer was deoxygenated. Deoxygenated 5N NaOH (284 mL) was added. The mixture was vigorously stirred at ambient temperature for 6–10 h until 1% starting material remained. The aqueous layer was separated and heated at 90° C. for 12–16 h until none of the intermediate 1-(mercaptomethyl)cyclopropaneacetamide remained.

The reaction was cooled to 25°–30° C. and 930 mL of deoxygenated heptane was added. The mixture was acidified to pH 3.5–4.0 with 5M NaHSO$_4$ solution over 1 h with stirring and allowed to warm to 30° C. The layers were separated at 30° C. and the aqueous layer was backextracted with 310 mL heptane. The combined organic layers were concentrated to 180 mL.

The mixture was warmed to 34° C. to completely solubilize the product and then allowed to slowly cool to 25° C. over 1 h. The mixture was seeded at 30° C. After stirring at 25° C. for 1 h to ensure a good seed bed, the mixture was cooled to −5° C. over 3 h. After stirring at −5° C. for 30 minutes, the mixture was filtered and washed with 20 mL of cold heptane. The title compound was obtained as an off-white crystalline solid (34.3 g, 83%).

EXAMPLE 2

1-(((1(R)-(3-(2-(7-chloro-2-quinolinyl)ethenyl)-phenyl)-3-(2-(1-hydroxy-1-methylethyl) phenyl)propyl)thio) methyl)-cyclopropaneacetic acid dicyclohexylamine salt Step 1: To a 100 L reactor equipped with a mechanical stirrer, a thermocouple, a nitrogen inlet and an addition funnel were placed tetrahydrofuran (33 L) and 1-(mercaptomethyl)cyclopropaneacetic acid (1.317 kg, 7.938 mol). The mixture was stirred for 10 minutes to ensure complete dissolution. A clear, pale yellow solution resulted. The solution was cooled to −15°±2° C. and n-butyl lithium (1.56M in hexanes, 10.5 L, 16.38 mol) was added over 75 minutes, maintaining the temperature of the reaction mixture ←5° C. The slurry was aged at −5°±2° C. for 30 minutes.

Step 2: To a 50 L flask equipped with a stirrer, a thermocouple and a nitrogen inlet was placed tetrahydrofuran (20 L). The solvent was cooled to 0°–5° C. The mesylate of Example 6 (4.501 kg, 7.558 mol) was added via a powder funnel and tetrahydrofuran (2.5 L) was used to rinse the funnel. The mixture was stirred for 15 minutes to ensure complete dissolution. A clear, pale yellow solution resulted.

Step 3: The solution of the mesylate from Step 2 was transferred using a 0.25" o.d. polypropylene tubing under nitrogen pressure to the dianion slurry of Step 1 at −5°±2° C. over 75 minutes. The reaction solution was aged at −5°±2° C. for 8.5 hours. The reaction was quenched by pouring the clear, yellow reaction solution into a mixture of ethyl acetate (55 L) and 10% sodium chloride solution (55 L). The mixture was agitated for about 30 minutes and then the layers were allowed to separate. Two clear layers were obtained. The aqueous waste layer was drained off. The organic product layer was washed with 0.5M tartaric acid (36 L), then twice with water (36 L each time). The product solution was concentrated under vacuum to approx. 10 L. The product was dissolved in ethyl acetate (44 L) and the solution was allowed to equilibrate to room temperature (20°±2° C.).

Step 4: To the solution of the free acid in ethyl acetate (54 L) in 2×100 L, 3-necked flask equipped with a mechanical stirrer, a thermocouple, a nitrogen inlet and an addition funnel was added dicyclohexylamine (1.8 L). The clear solution was seeded with the dicyclohexylamine salt of the title compound (14 g). The resulting mixture was aged for about an hour, by which time a thick slurry resulted. A sample of the slurry was examined by cross-polarized microscopy to confirm crystallinity of the solid. Hexane (108 L) was slowly added over 2 hours maintaining a good agitation of the slurry. The slurry was aged at 20°±2° C. overnight. A sample of the slurry was examined by cross-polarized microscopy to confirm crystallinity of the solid. The slurry was suction filtered and the cake washed with cold (0°±2° C.) 1:2 ethyl acetate:hexanes (32 L). The product was dried under vacuum at 40°±2° C. with a nitrogen purge.

Isolated yield=4.745 kg (99 A %; 96 wt %; >99.8% ee; 79% yield). $^1$H NMR (CD$_3$OD) δ8.25 (d, 1H), 7.95 (d, 1H), 7.86 (d, 1H), 7.83 (d, 1H), 7.77 (d, 1H), 7.70 (bs, 1H), 7.54 (d, 1H), 7.49 (d, 1H), 7.46–7.35 (m, 4H), 7.12–7.03 (m, 3H), 4.87 (s, active H), 4.03 (dd, 1H), 3.11–3.05 (m, 3H), 2.84–2.81 (m, 1H), 2.64 (d, 1H), 2.52 (d, 1H), 2.38 (d, 1H), 2.29 (d, 1H), 2.23 (m, 1H), 2.00 (m, 4H), 1.82 (m, 4H), 1.66 (m, 2H), 1.51 (two s, 6H), 1.37–1.14 (m, 10H), 0.53–0.32 (m, 4H).

EXAMPLE 3

Sodium 1-(((1(R)-(3-(2-(7-chloro-2-quinolinyl)ethenyl)-phenyl)-3-(2-(1-hydroxy-1-methylethyl)phenyl) propyl)thio)methyl)cyclopropaneacetate Toluene (1000 mL) and water ((950 mL) were placed in a 12 liter extractor equipped with an overhead stirrer, a thermocouple, a nitrogen inlet and an addition funnel. With good mixing of the solvents, solid dicyclohexylamine salt of Example 7 (64.3 g, 82.16 mmol) was added via a powder funnel and toluene (260 mL) was used to rinse in the remaining solid. To the well stirred suspension, acetic acid (2M, 62 mL, 124 mmol) was added at room temperature. After approximately 10 minutes stirring was stopped. Two clear phases (yellow organic layer and colorless aqueous layer) resulted, and the aqueous waste layer was drained off. Water (950 mL) was charged to the extractor and the layers were mixed thoroughly for approx. 10 minutes. The agitation was stopped and the aqueous waste layer was drained off.

To the organic layer (1270 mL) containing the free acid a titrated solution of sodium hydroxide in 1% aqueous ethanol (aqueous without ethanol (0.486M, 169 mL, 82.13 mmol) was added in a steady stream over 10 minutes at room temperature under a nitrogen atmosphere. After 10 minutes age, the clear solution of the desired sodium salt was filtered through a pad of solkafloc using toluene (100 ml) for transfer and cake wash.

The clear filtrate was transferred under nitrogen to a 3 liter, 3-necked flask equipped with an overhead stirrer, a thermocouple, a nitrogen inlet and a distillation head. The solution was concentrated under vacuum to about 400 ml (ca. 40 mm Hg,≦40° C.). The distillation head was replaced with a reflux condenser and an addition funnel. The concentrate was maintained at 40°±2° C. and acetonitrile (400 mL) was added over 20 minutes. The clear solution was seeded with 0.5 g of the crystalline sodium salt, and the resulting mixture was maintained at 40°±2° C. for 1.5 hours, by which time a good seed bed was established.

Acetonitrile (400 ml) was slowly added over 20 minutes, maintaining the batch temperature at 40°±2° C. The white suspension was stirred at 40°±2° C. for 1 hour and acetonitrile (400 mL) was slowly added over 20 minutes. The slurry was aged at 40°±2° C. for 12 hours. A sample of the suspension was examined by cross-polarized microscopy to confirm crystallinity of the solid. The suspension was cooled to RT and aged at RT for 1 hour. The crystalline sodium salt was suction filtered through a sintered funnel under nitrogen. The cake was washed with acetonitrile (400 ml). The crystalline sodium salt cake was broken up in a nitrogen glove bag and dried under vacuum with nitrogen bleed at 40°–45° C. The product (49 g, 80.59 mmol, 98% yield) was packaged in a well sealed brown bottle under nitrogen. The reaction mixture and the isolated product were protected from light at all times.

HPLC assay of the sodium salt: >99.5 A %. Chiral purity: 99.8% ee. $^1$H NMR (CD$_3$OD) δ8.23 (d, 1H), 7.95 (d, 1H), 7.83 (d, 1H), 7.82 (d, 1H), 7.75 (d, H), 7.70 (bs, 1H), 7.54 (dt, 1H), 7.46 (dd, 1H), 7.42-7.35 (m, 3H), 7.37 (d, 1H), 7.14-7.00 (m, 3H), 4.86 (s, active H), 4.03 (dd, 1H), 3.09 (m, 1H), 2.82 (m, 1H), 2.66 (d, 1H), 2.52 (d, 1H), 2.40 (d, 1H), 2.30 (d, 1H), 2.24-2.14 (m, 2H), 1.51 (two s, 6H), 0.52-0.32 (m, 4H).

EXAMPLE 4

1-(((1(R)-(3-(2-(7-chloro-2-quinolinyl)ethenyl)-phenyl)-3-(2-(1-hydroxy-1-methylethyl)phenyl)propyl)thio)methyl) cyclopropaneacetic acid dicyclohexylamine salt crystallized from toluene/heptane Step 1:

To a 2.0 L reactor equipped with a mechanical stirrer, a thermocouple, a nitrogen inlet and an addition funnel were placed tetrahydrofuran (132 ml) and 1-(mercaptomethyl)cyclopropaneacetic acid (9,830 g, 65.98 mmol). The mixture was stirred for 10 minutes to ensure complete dissolution. A clear, pale yellow solution resulted.

The solution was cooled to −15°±2° C. n-Butyl lithium (1.70M in hexanes, 79.6 ml, 135.26 mmol) was added over 30 minutes, maintaining the temperature of the reaction mixture ←5° C. The slurry was aged at −5°±2° C. for 30 minutes.

Step 2:

To a 250 ml flask, equipped with a stirrer, a thermocouple and a nitrogen inlet were placed mesylate of Example 6 (36.52 g, 62.68 mmol) and THF (106 ml). The solution was cooled to 0°–5° C. The mixture was stirred for 15 minutes to ensure complete dissolution. A clear, pale yellow solution resulted.

Step 3:

The solution of the mesylate of Step 2 was transferred via cannula to the dianion slurry of Step 1 at −5°±2° C. over 5 minutes. The reaction solution was aged at 0°±2° C. for 15 hours. The heterogeneous, yellow reaction solution was quenched by addition to a solution of 10% brine (200 ml). The mixture was agitated for about 10 minutes and the layers were allowed to separate. The organic product layer was washed with 0.5M tartaric acid (280 ml), then washed with water (2×120 ml).

The product solution was transferred to a 500 ml 1-neck flask. To this solution 250 ml of toluene was added along with dicyclohexylamine (14.44 ml, 72.60 mmol). This clear solution was treated with Darco G-60 (1.8 g) and the mixture was stirred under nitrogen for an hour. The mixture was filtered through a bed of solka floc (12 g) using toluene (20 mL) for rinse and transfer. The filtrate and wash were combined and concentrated under vacuum to ~200 ml. Another 200 ml of toluene was then added and the volume was reduced to 200 ml again.

The above solution was diluted to 640 ml with toluene and transferred to a 2.0 L, 3-necked flask equipped with a mechanical stirrer, a thermocouple, a nitrogen inlet, and an addition funnel. The clear solution was seeded with dicyclohexylamine salt of the title compound (200 mg) previously crystallized from toluene/heptane. The resulting mixture was aged for about 3 hours, by which time a thick slurry resulted. A sample of the slurry was examined by cross-polarized microscopy to confirm crystallinity of the solid. Heptane (280 ml) was slowly added over 2 hours maintaining a good agitation of the slurry. The slurry was aged at 20°±2° C. overnight. A sample of the slurry was examined by cross-polarized microscopy to confirm crystallinity of the solid. The slurry was suction filtered and the cake washed with 1:1 heptane:toluene (200 ml). The product was dried under vacuum at 40°±2° C. with a nitrogen purge. Isolated yield of the title dicyclohexylamine salt=40.39 g (purity: 99.3 A %, >99.8% ee; 80.6% yield).

In case the purity of the product is below about 99%, the product may be further purified by swishing with toluene/heptane. For example, the DCHA salt (98.6 A % purity, 10.03 g) was swished with toluene/heptane (1.5:1, 300 ml) at room temperature for 5 hours. The slurry was filtred and dried as earlier to obtain further purified DCHA salt (9.63 g, 99.4 A %).

EXAMPLE 5

Alternative method for the preparation of sodium 1-(((1(R)-(3-(2-(7-chloro-2-quinolinyl)ethenyl)phenyl)-3-(2-(1-hydroxy-1-methylethyl)phenyl)propyl)thio)methyl) cyclopropaneacetate To a 1 L round bottom, 3 neck flask equipped with overhead stirrer and nitrogen bubbler were charged 285 ml of toluene, 85 ml THF, and 215 ml deionized water. To this was charged 25.0 grams of solid DCHA salt of 1-(((1(R)-

(3-(2-(7-chloro-2-quinolinyl) ethenyl)phenyl)-3-(2-(1-hydroxy-1-methylethyl)phenyl)propyl)thio) methyl)cyclopropaneacetic acid (97.3 wt % purity). To the resulting slurry was charged 23.3 ml of 2.04M aqueous acetic acid.

The flask was purged 3 times with nitrogen and vacuum and left with a nitrogen blanket. The two phase mixture was agitated for 15 minutes. The agitation was stopped and the mixture was transferred to a 1000 ml separatory funnel, the batch was settled for 15 minutes, and the aqueous layer was cut off.

The organic layer was washed with deionized water (2×215 mL) as above, and the organic layer was returned to a 1L round bottom flask and purged 3 times with nitrogen and vacuum. A 0.500M solution of NaOH in 1% aqueous ethanol (63.3 mL) was added to the organic layer. At the end of the addition one clear phase was present. The resulting solution was filtered through a 0.45 µm nylon membrane filter (precoated with 2.5 g of Solka Floc) into a second 1 L round bottom flask. The funnel was rinsed with 50 ml of toluene which was combined with the initial filtrate. The resulting solution was vacuum distilled (T≦40° C.) to a volume of ~165 ml. Toluene (165 ml, 0.45 µm filtered) was added and the solution concentrated to 165 ml. The toluene dilution/concentration step was repeated to provide a solution of 165 ml final volume.

A slurry seedbed was prepared in a 1 liter resin kettle equipped with overhead stirrer and nitrogen bubbler. To the resin kettle were charged 32 ml of 0.45 µm filtered toluene, 64 ml of 0.45 µm filtered acetonitrile, and 3.86 g of title sodium salt seed.

The sodium salt concentrate (165 ml) and sieve dried, 0.45 µm filtered acetonitrile (330 ml, KF<100 µg/ml) were charged simultaneously to the seedbed over 8 hours via two syringe pumps. The seedbed temperature was maintained at 20° C. during the addition, and the flowrates were matched in order to maintain the crystallizer solvent ratio at ~2:1 acetonitrile:toluene. The microscopic appearance of the slurry and the supernatant concentration were monitored throughout the simultaneous addition. After the completion of the addition, the resulting slurry was aged overnight at 20° C. (16 hours).

The crystallized slurry was vacuum filtered under nitrogen insertion, leaving behind ~100 ml of slurry to serve as the seedbed for a subsequent crystallization. The filtered cake was washed with 238 ml of sieve dried, 0.45 µm filtered acetonitrile (KF<100 µg/ml). The resulting cake was dried in a vacuum oven at 40°–45° C. for 48 hours. A total of 17.75 g of sodium salt were recovered (99.3 wt %).

A second sodium salt formation and crystallization cycle was performed the same as described above, using the seedbed left from cycle #1. After the completion of the cycle #2 crystallization, the entire slurry was filtered without leaving behind a seedbed. The total product isolated from cycle #2 was 20.38 g (99.7 wt %). The overall material balance for the two cycles was 95.2%, with a yield of 92.1% (corrected for sampling the mechanical losses due to holdup in the crystallizer).

What is claimed is:

1. A process for preparing a compound of the formula

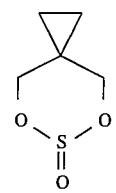

which comprises:
(a) contacting 1,1-cyclopropanedimethanol with dialkylsulfite in the presence of an acid or a base; and
(b) removing from the reaction mixture the alcohol reaction by-product.

2. A process of claim 1 wherein the reaction is carried out in the presence of a base.

3. A process of claim 2 wherein said dialkylsulfite is diisopropylsulfite.

4. A process of claim 2 wherein said base is sodium t-butoxide.

5. A process of claim 2 wherein said dialkylsulfite is diisopropylsulfite, said base is sodium t-butoxide, and said reaction by-product is removed by distillation.

6. A process of claim 1 further comprising: conducting the reaction in dimethylformamide.

7. A process for preparing 1-(hydroxymethyl)cyclopropaneacetonitrile which comprises:
(a) contacting 1,1-cyclopropane-dimethanol with dialkylsulfite in an inert polar organic solvent and in the presence of a base;
(b) removing from the reaction mixture the alcohol reaction by-product; and
(c) adding directly to the product of step (b) sodium cyanide and sodium iodide to provide the desired product.

8. A process of claim 7 wherein said dialkylsulfite is diisopropylsulfite.

9. A process of claim 7 wherein said solvent is dimethylformamide.

10. A process of claim 7 wherein said base is sodium t-butoxide.

11. A process of claim 7 wherein said dialkylsulfite is diisopropylsulfite, said solvent is dimethylformamide, said base is sodium t-butoxide, and said reaction by-product is removed by distillation.

12. A process for preparing 1-(thiomethyl)cyclopropaneacetic acid which comprises:
(a) contacting 1,1-cyclopropanedimethanol with dialkylsulfite in an inert polar organic solvent and in the presence of a base;
(b) removing from the reaction mixture the alcohol reaction by-product;
(c) adding directly to the product of step (b) sodium cyanide and sodium iodide to provide 1-(hydroxymethyl)cyclopropaneacetonitrile;
(d) converting the hydroxy group of the product of step (c) into a sulfonate leaving group;
(e) contacting the product of step (d) with thiolacetic acid and an amine base to provide 1-(acetylthiomethyl)cyclopropaneacetonitrile; and
(f) hydrolyzing the product of step (e) in a biphasic solvent system.

13. A process of claim 12 wherein said dialkylsulfite is diisopropylsulfite.

14. A process of claim 12 wherein said solvent of step (a) is dimethylformamide.

15. A process of claim 12 wherein said base in step (a) is sodium t-butoxide.

16. A process of claim 12 wherein said dialkylsulfite is diisopropylsulfite, said solvent in step (a) is dimethylformamide, said base is sodium t-butoxide, said reaction by-product of step (b) is removed by distillation, and said amine base of step (c) is triethylamine.

\* \* \* \* \*